United States Patent
Pan et al.

(10) Patent No.: US 11,207,304 B2
(45) Date of Patent: Dec. 28, 2021

(54) METHODS OF ADMINISTERING ANTI-FIBROTIC THERAPY

(71) Applicant: GENENTECH, INC., South San Francisco, CA (US)

(72) Inventors: Lin Pan, San Francisco, CA (US); Dorothy Sze-Wing Cheung, San Francisco, CA (US); Jeffrey Mark Harris, San Francisco, CA (US); Indiana Strombom, San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 16/465,015

(22) PCT Filed: Nov. 29, 2017

(86) PCT No.: PCT/US2017/063549
§ 371 (c)(1),
(2) Date: May 29, 2019

(87) PCT Pub. No.: WO2018/102323
PCT Pub. Date: Jun. 7, 2018

(65) Prior Publication Data
US 2019/0321344 A1     Oct. 24, 2019

Related U.S. Application Data

(60) Provisional application No. 62/432,425, filed on Dec. 9, 2016, provisional application No. 62/428,163, filed on Nov. 30, 2016.

(51) Int. Cl.
*A61K 31/437* (2006.01)
*A61K 31/4439* (2006.01)

(52) U.S. Cl.
CPC ........ *A61K 31/437* (2013.01); *A61K 31/4439* (2013.01)

(58) Field of Classification Search
CPC .............. A61K 31/437; A61K 31/4439; A61K 31/4355; A61P 11/00; A61P 29/00; A61P 37/00
USPC .......................................... 546/201; 514/303
See application file for complete search history.

(56) References Cited

FOREIGN PATENT DOCUMENTS

WO    WO-2015/153683 A1    10/2015

OTHER PUBLICATIONS

Adithan, Food and drug bioavailability, Indian J. Med. Res., 121 (5):631-3 (May 2005).
International Application No. PCT/US2017/063549, International Search Report and Written Opinion, dated Apr. 5, 2018.
National Kidney Foundation, K/DOQI Clinical Practice Guidelines for Chronic Kidney Disease (2002).
Winstanley et al., The effects of food on drug bioavailability, Br. J. Clin. Pharmacol., 28(6):621-8 (Dec. 1989).
"Guidance for Industry Food-Effect Bioavailability and Fed Bioequivalence Studies", Guidance for Industry, U.S. Department of Health and Human Services, Food and Drug Administration Center for Drug Evaluation and Research (Dec. 2002).

(Continued)

*Primary Examiner* — Taylor V Oh
(74) *Attorney, Agent, or Firm* — Marshall, Gerstein & Borun LLP

(57) ABSTRACT

The present disclosure relates to methods of administering Compound I for treating fibrotic disorders, inflammatory disorders or autoimmune disorders.

20 Claims, 2 Drawing Sheets

MAD: Multiple Ascending Dose
Mean Change for Creatinine Levels (mg/dl) Over Time in Phase 1

*Number of subjects in cohort with change ≥ 0.3 mg/dL in creatinine level relative to baseline

(56) References Cited

OTHER PUBLICATIONS

Hino et al., Drug interaction (34, Drug interaction of food and medicine), Journal of Okayama Medical Association, 127:245-9 (2015).
Japanese Patent Application No. 2019-524383, Notice of Reasons for Rejection, dated Sep. 3, 2021.

METHODS OF ADMINISTERING ANTI-FIBROTIC THERAPY

BACKGROUND

This is the U.S. National Stage pf PCT/US2017/063549, filed Nov. 29, 2017, which claims the benefit under 35 U.S.C. § 119(e) of U.S. Provisional Patent Application Nos. 62/428,163, filed Nov. 30, 2016, and 62/432,425, filed Dec. 9, 2016, and the disclosures thereof are hereby incorporated by reference herein.

BACKGROUND

Field

The present disclosure relates to methods of administering Compound I.

Description

Compound I is an orally available small molecule having the structure:

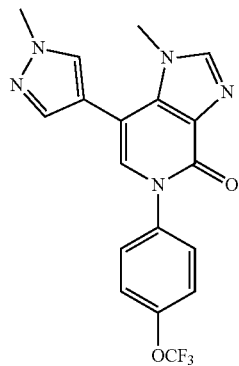 [SMILES: Cn1cc(-c2cn(-c3ccc(OC(F)(F)F)cc3)c(=O)c3ncn(C)c23)cn1]

Compound I has therapeutic value in several different indications that display fibrotic pathophysiology, such as idiopathic pulmonary fibrosis (IPF).

Idiopathic pulmonary fibrosis is a disease of unknown etiology that occurs mainly in middle-aged and elderly patients, which is characterized by progressive fibrosis of the lung, leading to pulmonary insufficiency and death. Because fibrosis has long been considered to be a clinically irreversible process, treatments have traditionally been focused on managing the symptoms and complications, with little hope of significantly slowing progression of the condition. For many years, mainstay treatments have been typically anti-inflammatory, immunosuppressive, and anti-oxidant agents. The effectiveness of these therapies in the treatment of IPF and other fibrotic conditions appears to be minimal and variable, and their side effects are often poorly tolerated by patients.

New treatment options have only recently become available. Both pirfenidone and nintedanib have been approved for use in the treatment of IPF. Current research efforts to develop new anti-fibrotic agents are targeting multiple mechanisms proposed to be linked to the underlying molecular pathogenic processes. This changing landscape has raised hopes and expectations for what might be achievable with new single agents or combination therapies targeting additional pathways.

SUMMARY

Unexpected food effects have now been identified for Compound I therapies. Described herein are clinical trials that reveal that the administration of Compound I with food unexpectedly increases the bioavailability of the drug, indicating a positive food effect. For example, the administration of Compound I with either a high fat or a low fat meal improves the $C_{max}$ and AUC of the drug, thereby improving the efficacy of the treatment.

Some embodiments of the present disclosure relate to methods of administering Compound I to treat a patient suffering from a fibrotic disorder, an inflammatory disorder, or an autoimmune disorder, comprising administering a therapeutically effective amount of Compound I in combination with food.

Some embodiments of the present disclosure relate to methods of increasing drug bioavailability in Compound I therapy to treat a subject suffering from a fibrotic disorder, an inflammatory disorder, or an autoimmune disorder, comprising: administering to a subject a therapeutically effective amount of Compound I with food, wherein the bioavailability of Compound I is increased compared to the bioavailability of the same amount of Compound I administered without food.

Some embodiments of the present disclosure relate to methods of providing Compound I therapy to a subject, comprising providing a therapeutically effective amount of Compound I to the subject; and advising the subject not to take a gastric acid reducing agent concomitantly with Compound I. In some embodiment, the gastric acid reducing agent is a proton pump inhibitor (PPI). Some embodiments of the present disclosure relate to methods of providing Compound I therapy to a subject, comprising providing a therapeutically effective amount of Compound I to the subject; and advising the subject that taking a PPI concomitantly with Compound I may require dose adjustment of Compound I. Some embodiments of the present disclosure relate to methods of providing Compound I therapy to a subject taking a PPI, comprising providing a therapeutically effective amount of Compound I to the subject taking a PPI; wherein the therapeutically effective amount of Compound I in the subject taking a PPI is greater than the therapeutically effective amount of Compound I in a subject not taking a PPI.

Some further embodiments of the present disclosure relate to methods for providing Compound I therapy, comprising administering a therapeutically effective amount of Compound I to a subject having an intra-gastric pH equal to or less than 4.

Some further embodiments of the present disclosure relate to methods of providing Compound I therapy to a subject, comprising evaluating the renal function of the subject; and administering a therapeutically effective amount of Compound I to the subject. In some embodiments, evaluating the renal function of the subject comprises determining the subject's creatinine clearance rate. In some embodiments, the renal function of the subject is evaluated prior to administering the therapeutically effective amount of Compound I to the subject. In some embodiments, the renal function of the subject is evaluated after administering the therapeutically effective amount of Compound I to the subject.

Some further embodiments of the present disclosure relate to methods of providing an anti-fibrotic therapy to a subject, comprising evaluating the renal function of the subject;

advising the subject to not take Compound I; and providing anti-fibrotic therapy other than Compound I.

Some additional embodiments of the present disclosure relate to kits comprising a pharmaceutical composition, prescribing information, and a container, wherein the pharmaceutical composition comprises a therapeutically effective amount of Compound I.

In any embodiment of the methods or kits described herein, the effective daily amount of Compound I is from about 1 mg to about 5000 mg per day, about 5 mg to about 2500 mg per day, or about 10 mg to about 2000 mg per day. In some further embodiments, the amount of Compound I administered is from about 25 mg to about 1600 mg per day. In some further embodiments, the amount of Compound I administered is about 25 mg, about 75 mg, about 200 mg, about 275 mg, about 400 mg, about 550 mg, about 575 mg, about 800 mg, about 1150 mg, or about 1600 mg per day, or in a range defined by any two of the preceding values.

In any embodiment of the methods described herein, the subject treated is suffering from a fibrotic disorder, in particular idiopathic pulmonary fibrosis (IPF).

DETAILED DESCRIPTION

Figure 1:
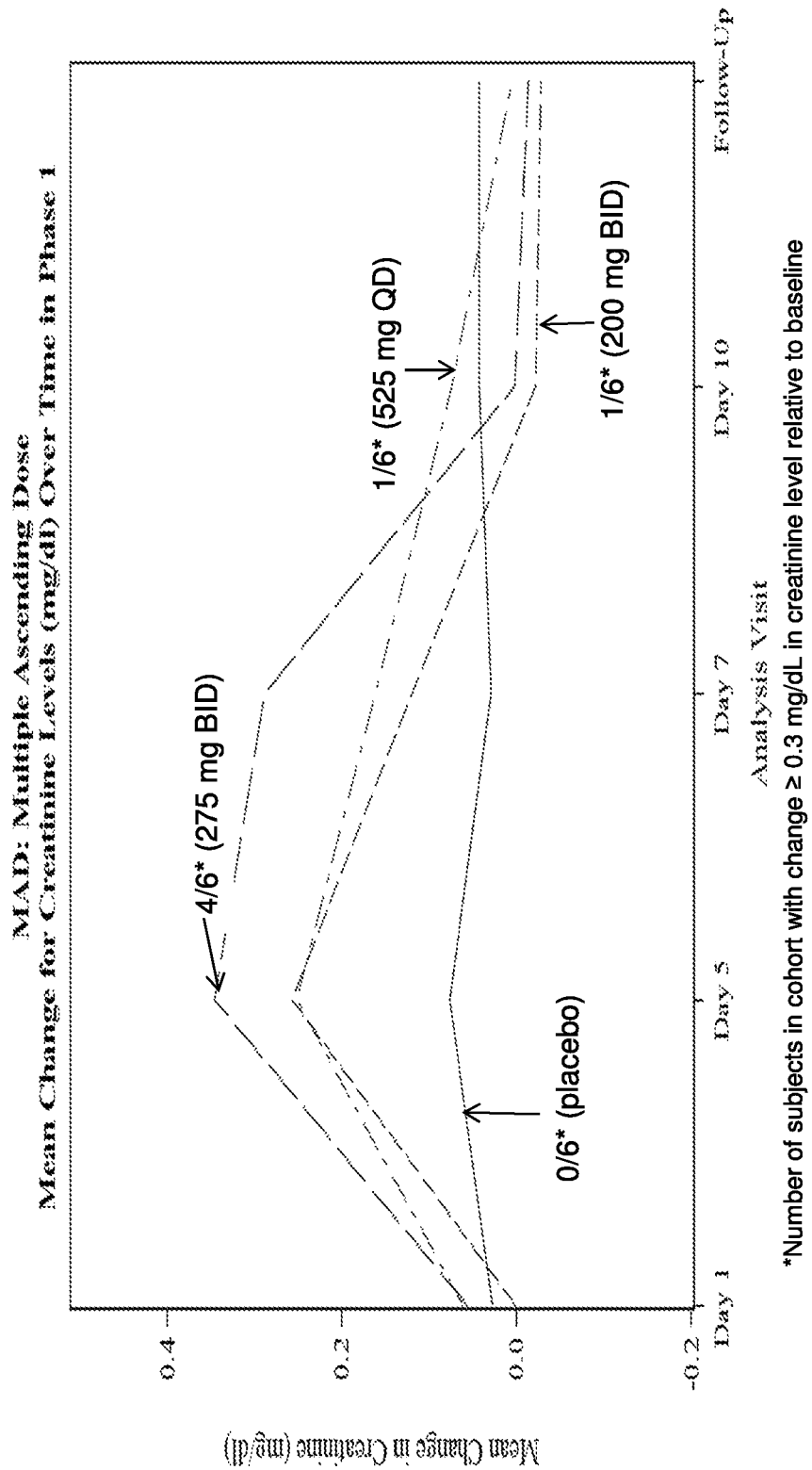
FIG. 1 illustrates the mean change in serum creatinine from a combined screening and pre-dose baseline in the Multiple Ascending Dose (MAD) part of the clinical study described herein.

Various embodiments described herein provide methods of increasing the bioavailability of Compound I by administering Compound I with food. Increasing the bioavailability of Compound I has various benefits. For example, increased bioavailability can result in more effective dosing. In some embodiments, more effective dosing allows for a lower dosage of Compound I to be administered to an individual. In some embodiments, administration of Compound I with food can also reduce the frequency and/or severity of adverse effects associated with Compound I, or other drugs.

The section headings used herein are for organizational purposes only and are not to be construed as limiting the subject matter described.

As used herein, common abbreviations are defined as follows:
AE Adverse event
$Ae_{0-12}$ amount of drug excreted in the first 12 hours
$Ae_{0-24}$ amount of drug excreted in the first 24 hours
ANOVA analysis of variance
AUC area under the concentration-time curve
BID Twice daily
CI Confidence interval
CLcr Creatinine clearance
$C_{max}$ Maximum plasma concentration
eGFR Estimated glomerular filtration rate
ESRD End stage renal disease
$fe_{0-12}$ Percentage of drug excreted in the first 12 hours
$fe_{0-24}$ Percentage of drug excreted in the first 24 hours
PK Pharmacokinetics
PPI Proton pump inhibitor
QD Once daily
$RA_{Auc}$ accumulation ratio based upon area under the plasma concentration time curve during the dosing interval
SAD Single ascending dose
Scr Serum creatinine
SD Standard deviation
$t_{1/2}$ Apparent plasma terminal elimination half life
TEAE Treatment-emergent adverse event
$T_{last}$ Time to last measurable concentration As used herein, the term "with food" is defined to mean, in general, the condition of having consumed food during the period between from about 1 hour prior to the administration of Compound I to about 2 hours after the administration of Compound I. In some embodiments, the food is a solid food with sufficient bulk and fat content that it is not rapidly dissolved and absorbed in the stomach. Preferably, the food is a meal, such as breakfast, lunch, or dinner. In some embodiments, the food is at least about 100 calories, about 200 calories, about 250 calories, about 300 calories, about 400 calories, about 500 calories, about 600 calories, about 700 calories, about 800 calories, about 900 calories, about 1000 calories, about 1250 calories, about 1500 calories.

As used herein, the term "high fat meal" refers to a meal where fat accounts for about 50% or more of the total calorie-content of the meal.

As used herein, the term "medium fat meal" refers to a meal where fat accounts for about 26-49% of the total calorie-content of the meal.

As used herein, the term "low fat meal" refers to a meal where fat accounts for about 25% or less of the total calorie-content of the meal.

The terms "without food," "fasted," or "on an empty stomach" are defined to mean the condition of not having consumed food within the time period of about 1 hour prior to the administration of Compound I to about 2 hours after the administration of Compound I. In some embodiments, food has not been consumed for about 10 hours, about 8 hours, about 6 hours, about 4 hours, about 2 hours prior to administration of Compound I.

The term "oral dosage form," as used herein, has its ordinary meaning as understood by those skilled in the art and thus includes, by way of non-limiting example, a formulation of a drug or drugs in a form administrable to a human, including pills, tablets, cores, capsules, caplets, loose powder, solutions, and suspensions.

The term "food effect," as used herein, refers to a phenomenon that can influence the absorption of drugs following administration. A food effect can be designated "negative" when absorption is decreased, or "positive" when absorption is increased and manifested as an increase in bioavailability (e.g., as reflected by AUC). Food effects can also refer to changes in maximum concentration ($C_{max}$), or the time to reach maximum concentration ($T_{max}$), independently of overall absorption. As a result, some drugs can preferably be taken in either fasted or fed conditions to achieve an optimum desired effect. As used herein, the terms "with food" and "fed" can be used interchangeably. As used herein, the terms "without food," "fasted," and "fasting" can be used interchangeably.

The term "renal impairment," as used herein, refers to impaired renal function as defined in the FDA Draft Guidance, Pharmacokinetics in Patients with Impaired Renal Function—Study Design, Data Analysis, and Impact on Dosing and Labeling (Mar. 22, 2010) summarized in the following table.

Classification of Renal Function Based on Estimated
GFR (eGFR) or Estimated Creatinine Clearance (CLcr)[a]

| Stage | Description[b] | eGFR[c] (mL/min/1.73 m$^2$) | CLcr[d] (mL/min) |
|---|---|---|---|
| 1 | Control (normal) GFR | ≥90 | ≥90 |
| 2 | Mild decrease in GFR | 60-89 | 60-89 |
| 3 | Moderate decrease in GFR | 30-59 | 30-59 |
| 4 | Severe decrease in GFR | 45-29 | 15-29 |
| 5 | End Stage Renal Disease (ESRD) | <15 not on dialysis Requiring dialysis | <15 not on dialysis Requiring dialysis |

[a]In some situations, collection of 24-hour urine samples for measurement of creatinine clearance, or measurement of clearance of an exogenous filtration marker, may provide better estimates of GFR than the prediction equations. The situations include determination of GFR for patients in the following scenarios: undergoing kidney replacement therapy; acute renal failure; extremes of age, body size, or muscle mass; conditions of severe malnutrition or obesity; disease of skeletal muscle; or on a vegetarian diet.
[b]Stages of renal impairment are based on K/DOQI Clinical Practice Guidelines for Chronic Kidney Disease (CKD) from the National Kidney Foundation in 2002; GFR: glomerular filtration rate;
[c]eGFR: estimate of GFR based on an MDRD equation;
[d]CLcr: estimated creatinine clearance based on the C-G equation.

The terms "pharmacokinetic profile" or "pharmacokinetics," as used herein, have their ordinary meaning as understood by those skilled in the art and thus include, by way of non-limiting example, a characteristic of the curve that results from plotting concentration (e.g. blood plasma, serum or tissue) of a drug over time, following administration of the drug to a subject. A pharmacokinetic profile thus includes a pharmacokinetic parameter or set of parameters that can be used to characterize the pharmacokinetics of a particular drug or dosage form when administered to a suitable population. In some embodiments, the suitable population may be defined as patients with renal impairment, patients with hepatic impairment, geriatrics, or pediatrics, etc. Various pharmacokinetic parameters are known to those skilled in the art, including area under the concentration vs. time curve (AUC), area under the concentration time curve from time zero until last quantifiable sample time ($AUC_{0-t}$), area under the concentration time curve from time zero extrapolated to infinity ($AUC_{0-\infty}$), area under the concentration time curve over the steady state dosing interval ($AUC_{ss}$) or from time zero to twelve hours ($AUC_{0-12}$) for twice-daily dosing, maximum concentration (e.g. blood plasma/serum) after administration ($C_{max}$), minimum concentration (e.g. blood plasma/serum) after administration ($C_{min}$), and time to reach maximum concentration (e.g. blood plasma/serum) after administration ($T_{max}$). $AUC_{last}$ indicates the area under the blood plasma concentration vs. time curve from the time of administration until the time of the last quantifiable concentration. Pharmacokinetic parameters may be measured in various ways known to those skilled in the art, e.g., for single dose or steady-state. Differences in one or more of the pharmacokinetic parameters (e.g., $C_{max}$) may indicate pharmacokinetic distinctness between two formulations or between two methods of administration.

The terms "patient" or "subject" refers to a human patient.

As used herein, the act of "providing" includes supplying, acquiring, or administering (including self-administering) a composition described herein.

As used herein, the term "administering" a drug includes an individual obtaining and taking a drug on their own. For example, in some embodiments, an individual obtains a drug from a pharmacy and self-administers the drug in accordance with the methods provided herein.

In any of the embodiments described herein, methods of treatment can alternatively entail use claims, such as Swiss-type use claims. For example, a method of treating a fibrotic disorder with a composition can alternatively entail the use of a composition in the manufacture of a medicament for the treatment of a fibrotic disorder, in particular IPF, or the use of a composition for the treatment of a fibrotic disorder, in particular IPF.

Those skilled in the art will understand that pharmacokinetic parameters may be determined by comparison to a reference standard using clinical trial methods known and accepted by those skilled in the art, e.g., as described in the examples set forth herein. Since the pharmacokinetics of a drug can vary from patient to patient, such clinical trials generally involve multiple patients and appropriate statistical analyses of the resulting data (e.g., ANOVA at 90% confidence). Comparisons of pharmacokinetic parameters can be on a dose-adjusted basis, as understood by those skilled in the art.

Some embodiments of the present disclosure relate to methods of administering Compound I to treat a subject suffering from a fibrotic disorder, an inflammatory disorder, or an autoimmune disorder, comprising administering a therapeutically effective amount of Compound I in combination with food.

The methods disclosed herein include administering Compound I to a patient or subject with food. The Compound I can be administered any time of day with food. For example, in some embodiments, the food can be consumed at any time during the period between from about 1 hour prior to the administration of Compound I to about 2 hours after the administration of Compound I. In some embodiments, the food can be consumed within the time period of about 1 hour, about 45 minutes, about 30 minutes, about 15 minutes, about 10 minutes, or about 5 minutes prior to the administration of Compound I. In some embodiments, the food can be consumed within the time period of about 5 minutes, about 10 minutes, about 15 minutes, about 30 minutes, about 45 minutes, about 1 hour, about 1.5 hours, or about 2 hours after the administration of Compound I. In some embodiments, the administration of Compound I to the patient is immediately after the consumption of food (e.g., within about 1 minute after food consumption) up to about 1 hour after food consumption. In some embodiments, Compound I is administered at substantially the same time as the consumption of the food.

In some embodiments, the amount of Compound I administered is from about 1 mg to about 5000 mg per day, about 5 mg to about 2500 mg per day, or about 10 mg to about 2000 mg per day. In some further embodiments, the amount of Compound I administered is from about 25 mg to about 1600 mg per day. In some further embodiments, the amount of Compound I administered is about 25 mg, about 75 mg, about 200 mg, about 275 mg, about 400 mg, about 550 mg, about 575 mg, about 800 mg, about 1150 mg, or about 1600 mg per day, or in a range defined by any two of the preceding values. In one embodiment, Compound I is administered 400 mg per day. In another embodiment, Compound I is administered 550 mg per day. In yet another embodiment, Compound I is administered 800 mg per day.

The dosing may be once or twice or three times daily, with one or more units per dose. In some embodiments, the effective daily intake of Compound I is administered as one, two, three, four, five, six, or more doses administered separately at appropriate intervals throughout the day. In some embodiments of the methods described herein, Compound I is administered once daily. In some other embodiments, Compound I is administered two or more times daily. In one embodiment, Compound I is administered twice daily. In another embodiment, Compound I is administered three times daily. In some embodiments, each dose comprises one, two, three or more unit dosage forms. For example, in some embodiments, one or more units are administered to the subject one or more times per day. In some embodiments, Compound I is administered as multiple doses spaced throughout the day and each dose comprises a therapeutically effective amount of Compound I. In some embodiments, Compound I is administered with food once per day.

In some embodiments, Compound I is administered to the subject in a unit dosage form comprising about 25 mg to about 500 mg, or about 50 mg to about 400 mg, or about 100 mg to about 200 mg Compound I per unit. In an embodiment, Compound I is administered to the subject in a unit dosage form comprising about 25 mg of Compound I per capsule or tablet. In another embodiment, Compound I is administered to the subject in a unit dosage form comprising about 200 mg of Compound I per capsule or tablet. As used herein, the term "unit dosage form," refers to physically discrete units suitable as unitary dosages for human and animal subjects, each unit containing a predetermined quantity of Compound I calculated in an amount sufficient to produce the desired effect in association with a pharmaceutically acceptable diluent, carrier or vehicle. In some embodiments, the unit dosage form is, for example, a pill, capsule, or tablet. In one embodiment, the unit dosage form is a tablet.

In some embodiments, the methods include administering a therapeutically acceptable amount of Compound I. The term "therapeutically effective amount" as used herein, refers to an amount of Compound I sufficient to treat, ameliorate, or prevent the identified disease or condition, or to exhibit a detectable therapeutic effect. The effect may be detected by any means known in the art. In some embodiments, the precise effective amount for a subject can depend upon the subject's body weight, size, and health; the nature and extent of the condition; and the therapeutic or combination of therapeutics selected for administration. Therapeutically effective amounts for a given situation may be determined by routine experimentation that is within the skill and judgment of the clinician.

In some embodiments of the methods described herein, the food is selected from a low fat meal, a medium fat meal or a high fat meal. In one embodiment, the food is a high fat meal.

In some embodiments, the methods comprise avoiding concomitant administration of a gastric acid-reducing therapeutic. In some embodiments, the gastric acid-reducing therapeutic is a proton pump inhibitor (PPI), a histamine 2 receptor antagonist (H2RA), and/or an antacid. In some embodiments, the gastric acid-reducing therapeutic is a PPI. In some embodiments, the PPI is selected from omeprazole, lansoprazole, pantoprazole, esomeprazole, rabeprazole, and dexlansoprazole. In some embodiments, the gastric acid-reducing therapeutic is an H2RA. In some embodiments, the H2RA is selected from cimetidine, famotidine, nizatidine, and ranitidine. In some embodiments, the gastric acid-reducing therapeutic is an antacid. In some embodiments, the antacid is selected from aluminum hydroxide/carbonate, calcium hydroxide/carbonate, and bismuth subsalicylate. In some embodiments, the methods comprise administering a re-acidification compound and Compound I to a patient receiving a gastric acid-reducing agent. In some embodiments, the re-acidification compound is selected from betaine hydrochloride and glutamic acid hydrochloride. In some embodiments, the methods comprise avoiding concomitant administration of a proton pump inhibitor (PPI), for example, avoiding concomitant administration of a PPI causing a 24-hour mean intra-gastric pH of equal or over about 6.0, 5.0, 4.0, 3.0, 2.0, or 1.0, or a range defined any of the two preceding values. In one embodiment, PPIs causing a 24-hour mean intra-gastric pH of equal or over 4 should be avoided. In another embodiment, PPIs causing a 24-hour mean intra-gastric pH of equal or over 3 should be avoided. In some further embodiments, the methods comprise avoiding administration of a proton pump inhibitor prior to or subsequent to the administration of Compound I.

Some embodiments of the present disclosure relate to methods of increasing drug bioavailability in Compound I therapy to treat a subject suffering from a fibrotic disorder, an inflammatory disorder, or an autoimmune disorder, comprising: administering to a subject a therapeutically effective amount of Compound I with food, wherein the bioavailability of Compound I is increased compared to the bioavailability of the same amount of Compound I administered without food.

An increase in bioavailability can be determined using one or more measures known to one of skill in the art, such as an increase in AUC or $C_{max}$, which can each independently be an increase that is, is about, is at least, or is at least about, 5%, 10%, 20%, 30%, 40%, 50%, 75%, 100%, 125%, 150%, 175%, 200%, 250%, 300%, 350%, 400%, 450%, 500%, 600%, 700%, or more, or within a range defined by any two of these values (e.g., 5%-500%, 10%-400%, or 20%-300%), wherein the increase is as compared to a reference treatment (e.g., a fasted state or a different fed state). In some embodiments, increasing the bioavailability of Compound I comprises increasing the maximal plasma concentration ($C_{max}$) or the extent of absorption ($AUC_{0-t}$ or $AUC_{0-\infty}$) of Compound I.

In some such embodiments, the increase in bioavailability comprises an increase in $C_{max}$ of Compound I in the range of about 10% to about 400%, about 15% to about 300%, or about 20% to about 250% when Compound I is taken with food compared to the same amount of Compound I taken during a fasted condition. In some further embodiments, the increase in $C_{max}$ of Compound I is in the range of about 20% to about 200%, about 40% to about 150%, or about 60% to about 125%. In one embodiment, the increase in $C_{max}$ of Compound I is about 64%. In another embodiment, the increase in $C_{max}$ is about 69%. In yet another embodiment, the increase in $C_{max}$ is about 126%.

In some such embodiments, the increase in bioavailability comprises an increase in $AUC_{0-t}$ of Compound I in the range of about 10% to about 400%, about 15% to about 300%, or about 20% to about 250% when Compound I is taken with food compared to the same amount of Compound I taken during a fasted condition. In some further embodiments, the increase in $AUC_{0-t}$ of Compound I is in the range of 20% to about 200%, about 25% to about 150%, or about 30% to about 125%. In one embodiment, the increase in $AUC_{0-t}$ of Compound I is about 37%. In another embodiment, the increase in $AUC_{0-t}$ is about 49%. In yet another embodiment, the increase in $AUC_{0-t}$ is about 114%.

In some such embodiments, the increase in bioavailability comprises an increase in $AUC_{0-\infty}$ of Compound I in the range of about 10% to about 400%, when 15% to about 300%, or about 20% to about 250% when Compound I is taken with food compared to the same amount of Compound I taken during a fasted condition. In some further embodiments, the increase in $AUC_{0-\infty}$ of Compound I is in the range of 20% to about 200%, about 25% to about 150%, or about 30% to about 125%. In one embodiment, the increase in $AUC_{0-\infty}$ of Compound I is about 35%. In another embodiment, the increase in $AUC_{0-\infty}$ is about 46%. In yet another embodiment, the increase in $AUC_{0-\infty}$ is about 103%.

Some embodiments of the present disclosure relate to methods of providing Compound I therapy to a subject, comprising providing a therapeutically effective amount of Compound I to the subject; and advising the subject not to take a proton pump inhibitor (PPI) concomitantly with Compound I. Some other embodiments of the present disclosure relate to methods of providing Compound I therapy to a subject, comprising providing a therapeutically effective amount of Compound I to the subject; and advising the subject not to take a proton pump inhibitor (PPI) prior to or subsequent to taking Compound I. Some embodiments of the present disclosure relate to methods of providing Compound I therapy to a subject, comprising providing a therapeutically effective amount of Compound I to the subject; and advising the subject not to take a proton pump inhibitor (PPI) concomitantly with Compound I, wherein the PPI causes a 24-hour intra-gastric pH of 4 or above. In some embodiments, PPIs should be avoided during Compound I therapy include those that cause a 24-hour mean intra-gastric pH of equal or over about 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0, or a range defined by any of the two preceding values. In one embodiment, PPIs causing a 24-hour mean intra-gastric pH of equal or over 4.0 should be avoided. In another embodiment, PPIs causing a 24-hour mean intra-gastric pH of equal or over 3.0 should be avoided. In one embodiment, the PPI is rabeprazole. In some embodiments, the methods further comprise advising the subject to take Compound I with food.

Some further embodiments of the present disclosure relate to methods for providing Compound I therapy, comprising administering a therapeutically effective amount of Compound I to a subject having an intra-gastric pH equal to or less than 4.0, 3.5, 3.0, 2.5, 2.0, 1.5, or 1.0, or a range defined by any of the two preceding values. Some further embodiments of the present disclosure relate to methods for providing Compound I therapy, comprising administering a therapeutically effective amount of Compound I to a subject having an intra-gastric pH equal to or less than 3.0. Some further embodiments of the present disclosure relate to methods for providing Compound I therapy, comprising administering a therapeutically effective amount of Compound I to a subject having an intra-gastric pH equal to or less than 2.0. In some such embodiments, the intra-gastric pH is the mean 24-hour intra-gastric pH. In some other embodiment, the intra-gastric pH is measured as the mean 12-hour intra-gastric pH, mean 8-hour intra-gastric pH, mean 6-hour intra-gastric pH, or mean 4-hour intra-gastric pH. In any of the embodiments described herein, Compound I may be administered with food.

Some further embodiments of the present disclosure relate to methods of providing Compound I therapy to a subject, comprising evaluating the renal function of the subject; and administering a therapeutically effective amount of Compound I to the subject. The purpose of this evaluation is to determine the renal effect of Compound I, for example, whether Compound I therapy would likely cause any kidney injury.

Acute kidney injury (AKI) is defined by Kidney Disease Improving Global Outcomes (KDIGO) (Kidney International Supplements (2012) 2, 8-12) as any of the following: increase in serum creatinine (SCr)≥0.3 mg/dL (≥26.5 μmol/L) within 48 hours; or increase in SCr to ≥1.5 times baseline, which is known or presumed to have occurred within the prior 7 days; or urine volume <0.5 mL/kg/h for 6 hours. AKI is staged for severity according to the following criteria.

| Stage | Serum creatinine (SCr) | Urine output |
|---|---|---|
| 1 | 1.5-1.9 times baseline<br>OR<br>≥0.3 mg/dL (≥26.5 μmol/L) increase | <0.5 mL/k/h for 6-12 h |
| 2 | 2-2.9 times baseline | <0.5 mL/kg/h for ≥12 h |
| 3 | 3 times baseline<br>OR<br>Increase in SCr ≥4 mg/dL (≥353.6 μmol/L)<br>OR<br>Initiation of renal replacement therapy<br>OR<br>In patients <18 years, decrease in eGFR to <35 mL/min per 1.73 m$^2$ | <0.3 mL/kg/h for ≥24 h<br>OR<br>Anuria for ≥12 h |

In some embodiments, evaluating the renal function of the subject comprises determining the subject's creatinine clearance rate. In some embodiments, the subject's creatinine clearance rate is evaluated prior to administering the therapeutically effective amount of Compound I to the subject. In some embodiments, the subject's creatinine clearance rate is evaluated after administering the therapeutically effective amount of Compound I to the subject. In some embodiments, the subject's creatinine clearance rate is evaluated prior to and after administering the therapeutically effective amount of Compound I to the subject. In some such embodiments, the subject has a creatinine clearance of ≥90 mL/min. In some other embodiments, the subject has a creatinine clearance of 60-89 mL/min. In some further embodiments, the subject has a creatinine clearance of 30-59 mL/min. In still some further embodiments, the subject has a creatinine clearance of 15-29 mL/min. In some embodiments, the subject does not have end stage renal disease (ESRD) requiring dialysis or have renal failure. In some embodiments, the method further comprises monitoring changes in the subject's serum creatinine (Scr) level after the administering of Compound I. In some further embodiments, the increase in the subject's Scr after administration of Compound I is monitored. In one particular embodiment, an increase in the subject's Scr ≥0.3 mg/dL from baseline is measured. In another embodiment, a percent increase in the subject's Scr ≥30% from baseline is measured. In some embodiments, the methods further comprises adjusting the amount of Compound I or discontinuing Compound I therapy, for example, if the percent change in the subject's Scr from baseline is over 30%, 40%, 50%, 60%, 70%, 80%, 90%, 100%, 110%, 120%, 130%, 140%, 150%, 160%, 170%, 180%, 190%, or 200%. Alternatively, adjusting the amount of Compound I or discontinuing Compound I therapy may be required if the increase in the subject's Scr from baseline is over 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, or 4.0 mg/dL. In some embodiments, the methods further comprise advising the subject to discontinue Compound I therapy.

Some further embodiments of the present disclosure relate to methods of providing an anti-fibrotic therapy to a subject, comprising evaluating the renal function of the subject; advising the subject to not take Compound I; and providing anti-fibrotic therapy other than Compound I. In some embodiments, the subject's renal function is evaluated prior to providing an anti-fibrotic therapy to a subject. In some embodiments, the subject's renal function is evaluated after providing an anti-fibrotic therapy to a subject. In some embodiments, the subject's renal function is evaluated prior to and after providing an anti-fibrotic therapy to a subject.

In any embodiment of the methods described herein, the subject is suffering from a fibrotic disorder. In one particular embodiment, the subject is suffering from idiopathic pulmonary fibrosis (IPF).

Some additional embodiments of the present disclosure relate to kits comprising a pharmaceutical composition, prescribing information, and a container, wherein the pharmaceutical composition comprises a therapeutically effective amount of Compound I. In some embodiments, the prescribing information advises a subject to take the pharmaceutical composition with food. In some further embodiments, the prescribing information advises the subject not to take a proton pump inhibitor (PPI) concomitantly with Compound I. In one embodiment, the prescribing information advises to avoid PPIs causing a 24-hour mean intra-gastric pH of equal or over 4.0. In another embodiment, the prescribing information advises to avoid PPIs causing a 24-hour mean intra-gastric pH of equal or over 3.0. In one embodiment, the PPI is selected from omeprazole, lansoprazole, pantoprazole, esomeprazole, rabeprazole, and dexlansoprazole. In one embodiment, the PPI is rabeprazole. The kit may include one or more unit dosage forms comprising Compound I. The unit dosage forms may be of an oral formulation. For example, the unit dosage forms may comprise pills, tablets, or capsules. The kit may include a plurality of unit dosage forms. In some embodiments, the unit dosage forms are in a container. In some embodiments, the dosage forms are single oral dosage forms comprising Compound I or pharmaceutically acceptable salts thereof. In some further embodiments, the prescribing information advises a health care provider to monitor for abnormalities and/or adverse reactions and consider dosage modification or discontinuation as needed in a subject with renal impairment. In some embodiments, abnormalities and/or adverse reactions comprise lab values outside the range of normal. In some embodiments, the lab value outside the range of normal is creatinine clearance. In some embodiments, the lab value outside the range of normal is serum creatinine. In some additional embodiments, the prescribing information advises a health care provider to not administer the pharmaceutical composition to a subject with end stage renal disease requiring dialysis. In some further additional embodiments, the prescribing information advises a health care provider that no dose adjustment is necessary in patients with mild renal impairment. In some further additional embodiments, the prescribing information advises a health care provider that the pharmaceutical composition should be used with caution in patients with moderate to severe renal impairment. In some further additional embodiments, the prescribing information advises a health care provider that the pharmaceutical composition should be used with caution in patients with moderate renal impairment. In some further additional embodiments, the prescribing information advises a health care provider to not administer the pharmaceutical composition to a subject with severe renal impairment.

The methods, compositions and kits disclosed herein may include information. The information may be in a form prescribed by a governmental agency regulating the manufacture, use, or sale of pharmaceuticals, which notice is reflective of approval by the agency of the form of the drug for human or veterinary administration. Such information, for example, may be the labeling approved by the U.S. Food and Drug Administration for prescription drugs, or the approved product insert. The information can include required information regarding dose and dosage forms, administration schedules and routes of administration, adverse events, contraindications, warning and precautions, drug interactions, and use in specific populations (see, e.g., 21 C.F.R. § 201.57 which is incorporated herein by reference in its entirety), and in some embodiments is required to be present on or associated with the drug for sale of the drug. In some embodiments, a kit is for sale of a prescription drug requiring the approval of and subject to the regulations of a governmental agency, such as the Food and Drug Administration of the United States. In some embodiments, the kit comprises the label or product insert required by the agency, such as the FDA, for sale of the kit to consumers, for example in the U.S. In preferred embodiments, the information instructs an individual to take Compound I, with food, preferably a meal. The information may also instruct an individual to avoid taking a proton pump inhibitor concomitantly, prior to or subsequent to taking Compound I. In some embodiments the information instructs a health care provider to monitor for abnormalities and/or adverse reactions and consider dosage modification or discontinuation as needed in a subject with renal impairment and/or not administer Compound I to a subject with end stage renal disease requiring dialysis. In some embodiments the information instructs a health care provider to monitor for abnormalities and/or adverse reactions and that no dose adjustment is necessary in patients with mild renal impairment. In some embodiments the information instructs a health care provider to monitor for abnormalities and/or adverse reactions and that Compound I should be used with caution in patients with moderate to severe renal impairment. In some embodiments the information instructs a health care provider to monitor for abnormalities and/or adverse reactions and that Compound I should be used with caution in patients with moderate renal impairment. In some embodiments the information instructs a health care provider to monitor for abnormalities and/or adverse reactions and not administer the pharmaceutical composition to a subject with severe renal impairment.

Some embodiments include information, preferably printed, that taking Compound I with food results in an increase in the bioavailability of Compound I or a pharmaceutically acceptable salt thereof compared to taking the same amount of Compound I or a pharmaceutically acceptable salt thereof without food.

Instructions and/or information may be present in a variety of forms, including printed information on a suitable medium or substrate (e.g., a piece or pieces of paper on which the information is printed), computer readable medium (e.g., diskette, CD, etc. on which the information has been recorded), or a website address that may be accessed via the internet. Printed information may, for example, be provided on a label associated with a drug product, on the container for a drug product, packaged with a drug product, or separately given to the patient apart from a drug product, or provided in manner that the patient can independently obtain the information (e.g., a website). Printed information may also be provided to a medical caregiver involved in treatment of the patient. In some embodiments, the information is provided to a person orally.

Some embodiments comprise a therapeutic package suitable for commercial sale. Some embodiments comprise a container. The container can be in any conventional shape or form as known in the art which is made of a pharmaceutically acceptable material, for example a paper or cardboard box, a glass or plastic bottle or jar, a re-sealable bag (e.g., to hold a "refill" of tablets for placement into a different container), or a blister pack with individual dosages for pressing out of the pack according to a therapeutic schedule. The container employed can depend on the exact dosage form involved, e.g., a conventional cardboard box would not generally be used to hold a liquid suspension. It is feasible that more than one container can be used together in a single package to market a single dosage form. For example, tablets may be contained in a bottle which is in turn contained within a box.

The information can be associated with the container, for example, by being: written on a label (e.g., the prescription label or a separate label) adhesively affixed to a bottle containing a dosage form described herein; included inside a container as a written package insert, such as inside a box which contains unit dose packets; applied directly to the container such as being printed on the wall of a box; or attached as by being tied or taped, e.g., as an instructional card affixed to the neck of a bottle via a string, cord or other line, lanyard or tether type device. The information may be printed directly on a unit dose pack or blister pack or blister card.

Pharmaceutical Compositions

Some embodiments include pharmaceutical compositions comprising: (a) a safe and therapeutically effective amount of Compound I described herein (including polymorphs, and solvates thereof), or pharmaceutically acceptable salts thereof; and (b) a pharmaceutically acceptable carrier, diluent, excipient or combination thereof.

The compounds useful as described above can be formulated into pharmaceutical compositions for use in treatment of various conditions or disorders. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to the selected compound useful as described above, some embodiments include compositions containing a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Pharmaceutically-acceptable carriers include, for example, solid or liquid fillers, diluents, hydrotropies, surface-active agents, and encapsulating substances. Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Per-oral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

It will be understood by those of skill in the art that numerous and various modifications can be made without departing from the spirit of the present invention. Therefore, it should be clearly understood that the embodiments of the present invention disclosed herein are illustrative only and are not intended to limit the scope of the present invention. Any reference referred to herein is incorporated by reference for the material discussed herein, and in its entirety.

EXAMPLE

A Phase 1, randomized, blinded, placebo-controlled safety, tolerability, and pharmacokinetic study of Compound I in 80 healthy adult subjects was conducted.

Methodology

This study was a randomized, blinded, placebo-controlled, ascending-dose study to evaluate the safety, tolerability, and pharmacokinetic (PK) of single (Part A) and multiple (Part B) doses of Compound I in healthy subjects. In addition, the effects of a standard high-fat breakfast, standard low-fat breakfast, and pretreatment and co-administration of a proton pump inhibitor (PPI) on the tolerability and PK of a single dose of Compound I were investigated in 2 groups in Part A. All subjects received their full dose of Compound I, administered as the appropriate number of either 25 or 200 mg tablets. The high fat breakfast comprised the following: total energy: 895 kcal; total fat: 61 g; total protein: 41 g; total carbohydrate: 46 g. The low fat breakfast comprised the following: total energy: 611 kcal; total fat: 14.7 g; total protein: 20.3 g; total carbohydrate: 106.3 g.

Part A—Single Ascending Dose (SAD):

In Part A, 56 subjects were studied in 6 groups (Groups A1 to A6) with each of Groups A1, A2, A3, A5, and A6 composed of 8 subjects (6 received Compound I, 2 received placebo) and Group A4 was composed of 16 subjects (12 received Compound I, 4 received placebo). The first dose group (A1) included a sentinel cohort of 2 subjects (1 subject received Compound I and 1 subject received placebo) dosed 48 hours in advance of the remainder of the group.

All subjects in Groups A1 through A6 participated in Treatment Period 1 and received the fasted treatment regimen. In Treatment Period 1, subjects resided at the Clinical Research Unit (CRU) from Day −1 (the day before dosing) to Day 4 (72 hours post-dose). In Treatment Period 1, all doses were administered on the morning of Day 1, after an overnight fast of at least 8 hours. In Groups A1, A2, A3, and A6, each subject received only a single dose of Compound I (25 mg in Group A1, 75 mg in Group A2, 200 mg in Group A3, and 1600 mg in Group A6) or placebo (per the randomization schedule) during the study.

For Group A4, doses (400 mg Compound I or placebo) during Treatment Period 1 were administered in a fasted state on the morning of Day 1. Doses in Treatment Period 2 were administered 30 minutes after starting, and within approximately 10 minutes of completing, a high-fat standard breakfast on the morning of Day 1. Doses during Treatment Period 3 were administered 30 minutes after starting, and within approximately 10 minutes of completing a low-fat standard meal on the morning of Day 1. Doses during Treatment Period 4 were administered on Day 1 after an overnight fast and following administration of a PPI (rabeprazole 20 mg) for 3 days (given as 3 daily [QD] doses, with the final PPI dose at 2 hours prior to study drug administration on Day 1). Subjects in Group A4 received the same Compound I or placebo treatment in all treatment periods, such that each subject received up to 4 single doses of Compound I or placebo.

For Group A5, doses (800 mg Compound I or placebo) during Treatment Period 1 were administered in a fasted state on the morning of Day 1, doses during Treatment Period 2 were administered 30 minutes after starting a low-fat standard breakfast on the morning of Day 1, and doses during Treatment Period 3 were administered on Day 1 after a low-fat meal and following administration of a PPI (rabeprazole 20 mg) for 3 days (given as 3 QD doses, with the final PPI dose at 2 hours prior to study drug administration on Day 1). Subjects in Group A5 received the same Compound I or placebo treatment in all treatment periods, such that each subject received up to 3 single doses of Compound I or placebo.

For Group A4, each subject participated in 3 additional treatment periods, each separated by a minimum of 7 days. Group A4 resided at the CRU from Day −1 to Day 4 of Treatment Periods 2, 3, and 4. For Group A5, each subject participated in 2 additional treatment periods, each separated by a minimum of 7 days. Group A5 resided at the CRU from Day −1 to Day 4 of Treatment Periods 2 and 3. All subjects returned for a Follow-up visit between 5 to 14 days after their final dose of study treatment.

In Part A, all doses in Treatment Period 1 were administered after an overnight fast of at least 8 hours. For the A4 cohort, in Treatment Periods 2 and 3, doses were administered 30 minutes after starting and approximately 10 minutes after completing a high- or low-fat breakfast. In Treatment Period 4, the dose was administered after an overnight fast and following administration of a PPI (PPI was comprised of 3 doses of rabeprazole 20 mg, starting on Day −2 and with the final dose 2 hours before Compound I administration on Day 1). For Group A5, doses during Treatment Period 2 were administered 30 minutes after starting and approximately 10 minutes after completing a low-fat standard breakfast on the morning of Day 1, and doses during Treatment Period 3 were administered on Day 1 after a low-fat meal and following administration of a PPI for 3 days (given as 3 QD doses, with the final PPI dose at 2 hours prior to study drug administration on Day 1).

A summary of the PK parameters of Compound I following single dose administration in the fasted state are summarized in Table 1.

TABLE 1

Mean Pharmacokinetic Parameters of Compound I by Treatment Group
(Part A - Single Doses Administered in the Fasting State)

| Parameter | Dose of Compound I | | | |
|---|---|---|---|---|
| | 25 mg (A1) (N = 6) | 75 mg (A2) (N = 6) | 200 mg (A3) (N = 6) | 400 mg (A4) (N = 12) |
| $AUC_{0-t}$ (hr*ng/mL) | 4550 (26.0) | 13000 (16.3) | 32300 (31.3) | 53800 (23.2) |
| $AUC_{0-t\ (norm)}$ (hr*ng/mL/(mg/kg)) | 13400 (25.2) | 12600 (31.8) | 12000 (33.6) | 9420 (31.0) |
| $AUC_{0-\infty}$ (hr*ng/mL) | 4600 (25.7) | 13000 (16.1) | 32600 (31.1) | 55100 (23.0) |
| $AUC_{0-\infty\ (norm)}$ (hr*ng/mL/(mg/kg)) | 13600 (24.9) | 12600 (31.6) | 12100 (33.5) | 9650 (30.0) |
| % $AUC_{extrap}^{a}$ (%) | 1.25 (0.493) | 0.486 (0.248) | 0.969 (0.434) | 2.37 (2.83) |
| $C_{max}$ (ng/mL) | 913 (28.0) | 2250 (17.1) | 3060 (31.9) | 4510 (13.1) |
| $C_{max\ (norm)}$ (ng/mL/(mg/kg)) | 2700 (29.8) | 2180 (31.4) | 1140 (30.1) | 790 (16.3) |
| $t_{max}^{b}$ (hr) | 1.50 (1.00-2.50) | 1.25 (1.00-2.00) | 1.75 (1.00-6.00) | 2.50 (1.00-4.25) |
| $t_{1/2}$ (hr) | 3.61 (43.8) | 5.02 (42.1) | 10.2 (14.5)$^c$ | 11.7 (54.5) |
| $\lambda_Z$ (hr$^{-1}$) | 0.192 (43.8) | 0.138 (42.1) | 0.0602 (34.0) | 0.0594 (54.5) |
| CL/F (mL/min) | 90.5 (25.7) | 96.0 (16.1) | 102 (31.1) | 121 (23.0) |
| CL/F$_{(norm)}$ ((mL/min)/kg) | 1.23 (24.9) | 1.32 (31.6) | 1.38 (33.5) | 1.73 (30.0) |
| $V_z$/F (L) | 28.3 (49.9) | 41.7 (53.8) | 102 (51.2) | 122 (54.1) |
| $V_z$/F$_{(norm)}$ (L/kg) | 0.384 (49.6) | 0.574 (64.0) | 1.37 (56.0) | 1.74 (64.8) |
| $Ae_{0-24}$ (mg) | 19.2 (8.7) | 54.8 (6.8) | 105 (21.3) | 133 (12.4) |
| $fe_{0-24}$ (%) | 76.9 (8.7) | 73.0 (6.8) | 52.5 (21.3) | 33.3 (12.4) |
| $CL_g$ (mL/min) | 70.5 (32.0) | 71.8 (19.7) | 63.5 (36.7) | 49.7 (21.2) |

| Parameter | Dose of Compound I | |
|---|---|---|
| | 800 mg (A5) (N = 6) | 1600 mg (A6) (N = 6) |
| $AUC_{0-t}$ (hr*ng/mL) | 74500 (27.1) | 73600 (47.6) |
| $AUC_{0-t\ (norm)}$ (hr*ng/mL/(mg/kg)) | 6700 (35.4) | 3090 (41.4) |
| $AUC_{0-\infty}$ (hr*ng/mL) | 78700 (29.7) | 86900 (61.2)$^d$ |
| $AUC_{0-\infty\ (norm)}$ (hr*ng/mL/(mg/kg)) | 7080 (38.0) | 3740 (51.2)$^d$ |
| % $AUC_{extrap}^{a}$ (%) | 5.17 (6.34) | 6.57 (4.04)$^d$ |
| $C_{max}$ (ng/mL) | 5910 (27.2) | 5580 (37.0) |
| $C_{max\ (norm)}$ (ng/mL/(mg/kg)) | 532 (28.9) | 235 (32.5) |
| $t_{max}^{b}$ (hr) | 1.75 (1.50-4.00) | 2.00 (1.00-4.00) |
| $t_{1/2}$ (hr) | 11.3 (44.6)$^d$ | 19.8 (25.8)$^d$ |
| $\lambda_Z$ (hr$^{-1}$) | 0.0433 (70.8) | 0.0351 (25.8)$^d$ |
| CL/F (mL/min) | 169 (29.7) | 307 (61.2)$^d$ |
| CL/F$_{(norm)}$ ((mL/min)/kg) | 2.35 (38.0) | 4.46 (51.2)$^d$ |
| $V_z$/F (L) | 234 (46.9) | 525 (47.8)$^d$ |
| $V_z$/F$_{(norm)}$ (L/kg) | 3.26 (49.8) | 7.62 (39.1)$^d$ |
| $Ae_{0-24}$ (mg) | 172 (23.0) | 145 (16.2) |
| $fe_{0-24}$ (%) | 21.5 (23.0) | 9.09 (16.2) |
| $CL_g$ (mL/min) | 48.5 (32.3) | 47.6 (50.5) |

$Ae_{0-24}$ = amount of GDC-3280 excreted over 24 hours; $AUC_{0-t}$ = area under the concentration-time curve (AUC) from time 0 to the last quantifiable concentration; $AUC_{0-\infty}$ = AUC extrapolated to infinity; % $AUC_{extrap}$ = percentage of AUC that is due to extrapolation from the last measurable concentration to infinity; $C_{max}$ = maximum observed plasma concentration; CL/F = apparent total plasma clearance; $CL_g$ = renal clearance; CV % = coefficient of variation; $fe_{0-24}$ = percentage of GDC-3280 excreted over 24 hours; N = number of subjects; norm = body weigh-normalized value; $t_{max}$ = time to maximum concentration; $t_{1/2}$ = apparent terminal elimination half-life; $V_z$/F = apparent volume of distribution during the terminal elimination phase; $\lambda_Z$ = apparent terminal elimination rate constant.
$^a$Arithmetic mean (arithmetic standard deviation).
$^b$Median (min-max).
$^c$n = 5.
$^d$n = 4.

Plasma concentration versus time plots for all doses were characterized by a rapid absorption phase. Median tmax results were generally similar across all doses, ranging from 1.3 to 2.5 hours, although there was a trend for increase in individual tmax ranges at the higher dose levels (200 to 1600 mg), with tmax occurring as late as 6 hours compared to the latest time point of 2.5 hours observed across the 25 and 75 mg doses. The mean t1/2 was similar for the 25 and 75 mg doses with values of 3.6 and 5.0 hours, respectively (range 2.1 to 9.6 hours), and increased to 10.2, 11.7, and 11.3 hours (range 4.1 to 27.0 hours) at the 200, 400, and 800 mg doses, respectively. At the highest dose level of 1600 mg, geometric mean t1/2 was 19.8 hours (range 13.8 to 24.0 hours).

Dose-normalized PK parameters were analyzed using ANOVA. Increase in systemic exposure, based on AUC and Cmax, between the 2 lowest dose levels (25 and 75 mg) are consistent with linear PK, with a 3-fold increase in dose resulting in 2.9-, 2.8-, and 2.5-fold increases in AUC0-$t$, AUC0-$\infty$, and Cmax, respectively for dose and body weight normalized AUC0-$t$, AUC0-$\infty$, and Cmax, respectively.

Between the higher dose levels of 200 to 800 mg, there was a trend for AUC and Cmax values to increase in a less than proportional manner. At the 800-mg dose level, a 32.0-fold increase in dose resulted in 16.4-, 17.1-, and 6.5-fold increases in $AUC_{0-t}$, $AUC_{0-\infty}$, and Cmax, respectively. Following the 1600 mg dose, there was no significant increase in AUC and Cmax compared to that of the 800 mg dose.

A summary of the PK parameters of Compound I following single dose administration of 400 and 800 mg in the fed and fasted states and with rabeprazole (PPI) are presented in Table 2 below.

TABLE 2

Mean Pharmacokinetic Parameters of Compound I by Treatment Condition (Part A - Single Doses)

| | Dose of Compound I 400 mg (A4) (N = 12) | | | |
|---|---|---|---|---|
| Parameter | Fasted | Fed, High-fat | Fed, Low-fat | +20 mg Rabeprazole QD x 3 Fasted |
| $AUC_{0-t}$ (hr*ng/mL) | 53800 (23.2) | 80200 (26.6) | 73700 (36.1) | 46500 (19.9) |
| $AUC_{0-t\ (norm)}$ (hr*ng/mL)/(mg/kg) | 9420 (31.0) | 14000 (33.3) | 12900 (40.0) | 8130 (29.0) |
| $AUC_{0-\infty}$ (hr*ng/mL) | 55100 (23.0) | 80300 (26.5) | 74200 (35.5) | 48100 (19.0) |
| $AUC_{0-\infty\ (norm)}$ (hr*ng/mL)/(mg/kg) | 9650 (30.0) | 14100 (33.3) | 13000 (39.4) | 8410 (27.0) |
| % $AUC_{extrap}{}^a$ (%) | 2.37 (2.83) | 0.213 (0.114) | 0.691 (0.659) | 3.25 (4.03) |
| $C_{max}$ (ng/mL) | 4510 (13.1) | 7620 (11.0) | 7420 (17.4) | 3770 (19.3) |
| $C_{max\ (norm)}$ (ng/mL/(mg/kg)) | 790 (16.3) | 1330 (17.7) | 1300 (20.5) | 660 (22.4) |
| $t_{max}{}^b$ (hr) | 2.50 (1.00-4.25) | 3.50 (1.50-6.00) | 2.50 (1.00-4.00) | 2.50 (1.50-4.00) |
| $t_{1/2}$ (hr) | 11.7 (54.5) | 8.05 (45.2) | 7.52 (48.1)$^c$ | 10.5 (62.8)$^c$ |
| $\lambda_Z$ (hr$^{-1}$) | 0.0594 (54.5) | 0.0861 (45.2) | 0.0852 (54.8) | 0.0603 (70.3) |
| CL/F (mL/min) | 121 (23.0) | 83.0 (26.5) | 89.8 (35.5) | 139 (19.0) |
| $CL/F_{(norm)}$ ((mL/min)/kg) | 1.73 (30.0) | 1.19 (33.3) | 1.28 (39.4) | 1.98 (27.0) |
| $V_z/F$ (L) | 122 (54.1) | 57.8 (58.6) | 63.3 (68.4) | 138 (71.3) |
| $V_z/F_{(norm)}$ (L/kg) | 1.74 (64.8) | 0.826 (68.5) | 0.904 (77.5) | 1.97 (84.7) |

| | Dose of Compound I 800 mg (A5) (N = 6) | | |
|---|---|---|---|
| Parameter | Fasted | Fed, Low-fat | +20 mg Rabeprazole QD x 3 Fed, Low-fat |
| $AUC_{0-t}$ (hr*ng/mL) | 74500 (27.1) | 159000 (36.4) | 122000 (21.6) |
| $AUC_{0-t\ (norm)}$ (hr*ng/mL)/(mg/kg) | 6700 (35.4) | 14300 (29.3) | 11000 (29.9) |
| $AUC_{0-\infty}$ (hr*ng/mL) | 78700 (29.7) | 160000 (36.5) | 124000 (20.7) |
| $AUC_{0-\infty\ (norm)}$ (hr*ng/mL)/(mg/kg) | 7080 (38.0) | 14400 (29.2) | 11100 (29.7) |
| % $AUC_{extrap}{}^a$ (%) | 5.17 (6.34) | 0.395 (0.410) | 1.27 (2.08) |
| $C_{max}$ (ng/mL) | 5910 (27.2) | 13300 (31.5) | 10000 (28.7) |
| $C_{max\ (norm)}$ (ng/mL/(mg/kg)) | 532 (28.9) | 1200 (21.7) | 900 (34.5) |
| $t_{max}{}^b$ (hr) | 1.75 (1.50-4.00) | 3.00 (2.50-4.00) | 3.00 (2.50-4.00) |
| $t_{1/2}$ (hr) | 11.3 (44.6)$^d$ | 8.74 (57.1) | 8.92 (43.8)$^e$ |
| $\lambda_Z$ (hr$^{-1}$) | 0.0433 (70.8) | 0.0793 (57.1) | 0.0666 (57.1) |
| CL/F (mL/min) | 169 (29.7) | 83.3 (36.5) | 108 (20.7) |
| $CL/F_{(norm)}$ ((mL/min)/kg) | 2.35 (38.0) | 1.16 (29.2) | 1.50 (29.7) |
| $V_z/F$ (L) | 234 (46.9) | 63.0 (78.2) | 97.2 (67.7) |
| $V_z/F_{(norm)}$ (L/kg) | 3.26 (49.8) | 0.876 (79.8) | 1.35 (61.6) |

$AUC_{0-t}$ = area under the concentration-time curve (AUC) from time 0 to the last quantifiable concentration; $AUC_{0-\infty}$ = AUC extrapolated to infinity; % $AUC_{extrap}$ = percentage of AUC that is due to extrapolation from the last measurable concentration to infinity; $C_{max}$ = maximum observed plasma concentration; CL/F = apparent total plasma clearance; $CL_R$ = renal clearance; $t_{max}$ = time to maximum concentration; CV % = coefficient of variation; N = number of subjects; norm = body weigh-normalized value; $t_{1/2}$ = apparent terminal elimination half-life; $V_z/F$ = apparent volume of distribution during the terminal elimination phase; $\lambda_Z$ = apparent terminal elimination rate constant.
$^a$Arithmetic mean (arithmetic standard deviation).
$^b$Median (min-max).
$^c$n = 11.
$^d$n = 4.
$^e$n = 5.

Food Effect

Following administration of 400 mg Compound I in the high-fat fed state, there was a delay in tmax of 1.0 hour (median tmax 3.5 hours, range 1.5 to 6.0 hours) compared to that of the low-fat fed and fasted states (median tmax 2.5 hours, range 1.0 to 4.3 hours). See Table 2. Following attainment of Cmax, plasma Compound I concentrations declined in a biphasic manner in both the fasted and fed states. Systemic exposure was higher in the high-fat fed state, with ratios of fed to fasted of 149.0%, 145.8%, and 168.9% for AUC0-$t$, AUC0-$\infty$, and Cmax, respectively (Table 3). Following a 400 mg Compound I dose in the low-fat fed state there was an increase in systemic exposure with ratios of fed to fasted of 137.1%, 134.7%, and 164.4% in AUC0-$t$, AUC0-$\infty$, and Cmax, respectively (Table 3). Statistical comparison of the high-fat to low-fat fed state at 400 mg Compound I indicated similar exposure with ratios of 108.7%, 108.2% and 102.7% for AUC0-$t$, AUC0-$\infty$, and Cmax, respectively (Table 3).

Following administration of 800 mg Compound I in the low-fat fed state, the median tmax was delayed by 1.25 hours. Systemic exposure to Compound I in the low-fat fed state, as measured by AUC0-$t$, AUC0-$\infty$, and Cmax increased, with ratios of fed to fasted of 214.0%, 203.3%, and 225.5%, respectively (Table 3).

Following administration of both 400 and 800 mg Compound I there was a trend for a slightly longer t1/2 in the fasted state with geometric mean t1/2 values of 11.7 and 11.3 hours, respectively. This is in comparison to the high- and low-fat states where geometric means ranged from 7.5 to 8.7 hours.

TABLE 3

Statistical Analysis of Pharmacokinetic Data of Compound I (Part A): Effect of High-fat, Low-fat and Fed States

| Parameters (Units) | n[b] | LS Means[a] 400 mg Compound I Fed, High-fat (Test) | n[b] | LS Means[a] 400 mg Compound I Fasted (Reference) | Test/ Reference[c] (%) | 90% Confidence Interval[d] (%) | $CV_W$[e] (%) |
|---|---|---|---|---|---|---|---|
| $AUC_{0-t}$ (hr*ng/mL) | 12 | 80200 | 12 | 53800 | 149.0 | (131.9, 168.4) | 17.8 |
| $AUC_{0-\infty}$ (hr*ng/mL) | 12 | 80300 | 12 | 55100 | 145.8 | (129.3, 164.3) | 17.5 |
| $C_{max}$ (ng/mL) | 12 | 7620 | 12 | 4510 | 168.9 | (151.8, 187.9) | 15.5 |

| Parameters (Units) | n[b] | 400 mg Compound I Fed, Low-fat (Test) | n[b] | 400 mg Compound I Fasted (Reference) | Test/ Reference[c] (%) | 90% Confidence Interval[d] (%) | $CV_W$[e] (%) |
|---|---|---|---|---|---|---|---|
| $AUC_{0-t}$ (hr*ng/mL) | 12 | 73700 | 12 | 53800 | 137.1 | (121.3, 154.9) | 17.;8 |
| $AUC_{0-\infty}$ (hr*ng/mL) | 12 | 74200 | 12 | 55100 | 134.7 | (119.5, 151.8) | 17.5 |
| $C_{max}$ (ng/mL) | 12 | 7420 | 12 | 4510 | 164.4 | (147.8, 182.9) | 15.5 |

| Parameters (Units) | n[b] | 400 mg Compound I Fed, High-fat (Test) | n[b] | 400 mg Compound I Fed, Low-fat (Reference) | Test/ Reference[c] (%) | 90% Confidence Interval[d] (%) | $CV_w$[e] (%) |
|---|---|---|---|---|---|---|---|
| $AUC_{0-t}$ (hr*ng/mL) | 12 | 80200 | 12 | 73700 | 108.7 | (96.2, 122.9) | 17.8 |
| $AUC_{0-\infty}$ (hr*ng/mL) | 12 | 80300 | 12 | 74200 | 108.2 | (96.0, 122.0) | 17.5 |
| $C_{max}$ (ng/mL) | 12 | 7620 | 12 | 7420 | 102.7 | (92.3, 114.3) | 15.5 |

| Parameters (Units) | n[b] | 400 mg Compound I Fed, Low-fat (Test) | n[b] | 400 mg Compound I Fasted (Reference) | Test/ Reference[c] (%) | 90% Confidence Interval[d] (%) | $CV_W$[e] (%) |
|---|---|---|---|---|---|---|---|
| $AUC_{0-t}$ (hr*ng/mL) | 6 | 159000 | 6 | 74500 | 214.0 | (167.3, 273.7) | 23.9 |
| $AUC_{0-\infty}$ (hr*ng/mL) | 6 | 160000 | 6 | 78700 | 203.3 | (157.8, 262.0) | 24.6 |
| $C_{max}$ (ng/mL) | 6 | 13300 | 6 | 5910 | 225.5 | (181.0, 280.9) | 21.2 |

$AUC_{0-t}$ = area under the concentration-time curve (AUC) from time 0 to the last quantifiable concentration; $AUC_{0-\infty}$ = AUC extrapolated to infinity; $C_{max}$ = maximum observed plasma concentration; $CV_W$ = within-subject coefficients of variation; LS = least squares.
[a]Least squares means from analysis of variance, calculated by transforming the natural-log means back to the linear scale (ie, geometric means).
[b]n is the number of observations in each treatment used in the model.
[c]Ratio of parameter means for natural log-transformed parameter (expressed as a percentage). Natural log-transformed ratios transformed back to the linear scale.
[d]90% confidence interval for ratio of parameter means of natural log-transformed parameter (expressed as a percentage). Natural log-transformed confidence limits transformed back to the linear scale.
[e]Within-subject coefficients of variation $CV_W(\%) = [\exp(mse) - 1]^{1/2} \times 100$ Proton Pump Inhibitor (PPI) Effect Following administration of a single 400 mg of Compound I in combination with 20 mg rabeprazole (QD×3) in the fasted state, Compound I was rapidly absorbed with a median $t_{max}$ of 2.5 hours (ranging from 1.5 to 4.0 hours) similar to the results when 400 mg of Compound I was administered alone (median $t_{max}$ was 2.5 hours, ranging from 1.0 to 4.3 hours). After reaching $C_{max}$, Compound I exhibited a biphasic decline with a similar geometric mean $t_{1/2}$ to that seen in the fasted state alone, 10.5 hours and 11.7 hours, respectively.

When a single dose of 400 mg Compound I was administered in combination with rabeprazole (20 mg QD×3) in the fasted state there were decreases in $AUC_{0-t}$, $AUC_{0-28}$, and $C_{max}$, with ratios of PPI co-administration to non-PPI co-administration of 86.4%, 87.2%, and 83.6%, respectively, with the 90% CIs excluding 100% in all comparisons (Table 4). The between-subject variability based on $AUC_{0-t}$, $AUC_{0-\infty}$, and $C_{max}$ was low following Compound I administration alone and when co-administered with rabeprazole in the fasted state, ranging from 19.0% to 23.2% for AUCs and 13.1% to 19.3% for $C_{max}$, respectively (Table 2).

When a single dose of 800 mg Compound I was co-administered with rabeprazole (20 mg, QD×3) in the low-fat fed state, there were decreases in $AUC_{0-t}$, $AUC_{0-\infty}$, and $C_{max}$, with ratios of PPI co-administration to non-PPI co-administration of 76.5%, 77.2%, and 75.0%, respectively (Table 4). These results show increased gastric pH (reduced gastric acid) leads to some impairment in absorption of Compound I. Time to maximum plasma concentration appeared delayed following the co-administration with rabeprazole, with a median $t_{max}$ of 3.0 hours (ranging from 2.5 to 4.0 hours) compared to 1.8 hours when administered alone (ranging from 1.5 to 4.0 hours).

Following single and multiple dose administration of Compound I at 200 mg BID, 275 mg BID, and 525 mg QD, Compound I was absorbed readily with median $t_{max}$ values of 2.3 to 3.5 hours post-dose on Day 1 and 2.8 to 4.0 hours post-dose on Day 7. On Day 7 plasma concentrations of Compound I declined in a generally biphasic manner following the attainment of $C_{max}$, with $t_{1/2}$ geometric mean values at the 200- and 275-mg BID dose levels of 4.9 hours (individual values ranging from 3.5 to 6.3 hours) and 5.6 hours (individual values ranging from 3.6 to 12.1 hours), respectively, and 6.3 hours (individual values ranging from 3.7 to 11.2 hours) at 525 mg QD (Table 5).

TABLE 4

Statistical Analysis of Pharmacokinetic Data of Compound I (Part A): PPI Effect

| Parameters (Units) | $n^b$ | LS Means[a] 400 mg Compound I Fasted + 20 mg Rabeprazole QD x 3 (Test) | $n^b$ | LS Means[a] 400 mg Compound I Fasted (Reference) | Test/ Reference[c] (%) | 90% Confidence Interval[d] (%) | $CV_W^e$ (%) |
|---|---|---|---|---|---|---|---|
| $AUC_{0-t}$ (hr*ng/mL) | 12 | 46500 | 12 | 53800 | 86.4 | (76.5, 97.6) | 17.8 |
| $AUC_{0-\infty}$ (hr*ng/mL) | 12 | 48100 | 12 | 55100 | 87.2 | (77.4, 98.3) | 17.5 |
| $C_{max}$ (ng/mL) | 12 | 3770 | 12 | 4510 | 83.6 | (75.2, 93.0) | 15.5 |
| Parameters (Units) | $n^b$ | 800 mg Compound I Fed, Low-fat + 20 mg Rabeprazole QD x 3 (Test) | $n^b$ | 800 mg Compound I Fasted (Reference) | Test/ Reference[c] (%) | 90% Confidence Interval[d] (%) | $CV_W^e$ (%) |
| $AUC_{0-t}$ (hr*ng/mL) | 6 | 122000 | 6 | 159000 | 76.5 | (59.8, 97.9) | 23.9 |
| $AUC_{0-\infty}$ (hr*ng/mL) | 6 | 124000 | 6 | 160000 | 77.2 | (59.9, 99.5) | 24.6 |
| $C_{max}$ (ng/mL) | 6 | 10000 | 6 | 13300 | 75.0 | (60.2, 93.5) | 21.2 |

$AUC_{0-t}$ = area under the concentration-time curve (AUC) from time 0 to the last quantifiable concentration; $AUC_{0-\infty}$ = AUC extrapolated to infinity; $C_{max}$ = maximum observed plasma concentration; $CV_W$ = within-subject coefficients of variation; LS = least squares.
[a]Least squares means from analysis of variance, calculated by transforming the natural-log means back to the linear scale (ie, geometric means).
[b]n is the number of observations in each treatment used in the model.
[c]Ratio of parameter means for natural log-transformed parameter (expressed as a percentage). Natural log-transformed ratios transformed back to the linear scale.
[d]90% confidence interval for ratio of parameter means of natural log-transformed parameter (expressed as a percentage). Natural log-transformed confidence limits transformed back to the linear scale.
[e]Within-subject coefficients of variation $CV_W(\%) = [\exp(\text{mse}) - 1]^{1/2} \times 100$ Part B—Multiple Ascending Dose (MAD):

In Part B, 24 subjects were studied in 3 groups (Groups B1 to B3), with each group consisting of 8 subjects (6 received Compound I and 2 received placebo). The dose, dosing frequency, duration, and dietary state for Part B were determined based on review of available PK, safety, and tolerability data from Parts A and B.

All doses in Part B were administered following administration of a low-fat meal. In Groups B1 and B3, Compound I (200 mg for Group B1, 275 mg for Group B3) or placebo was administered twice daily (BID) on Days 1 to 6 and once on the morning of Day 7. In Group B2, subjects received QD dosing with 525 mg Compound I or placebo on Days 1 to 7.

In Part B, each subject participated in 1 treatment period. Subjects resided at the CRU from Day −1 (the day before dosing) until the morning of Day 10 (72 hours after the final dose on Day 7). All subjects returned for a Follow-up visit between 5 to 14 days after their final dose.

In Part B, all doses were administered after a low-fat meal. On Day 1 and Day 7 (days with post-dose PK sampling), subjects started a low-fat breakfast 30 minutes prior to dosing and were given 15 minutes to complete their meal; dosing occurred approximately 15 minutes after completion of breakfast. On dosing Days 2 through 6, subjects were to complete their breakfast within an hour prior to dosing. For the evening doses, subjects were given a standard meal and completed their meal between 1 and 2 hours prior to dosing.

There was an approximately dose-proportional increase in $AUC_{0-\infty}$ between the 200 mg BID and 525 mg QD dosing regimens, with a 2.6-fold increase in dose resulting in a 2.5-fold increase in geometric mean $AUC_{0-\infty}$. For the 200- and 275-mg BID doses, there was a 1.2-fold increase in geometric mean $C_{max}$ for the 1.4-fold increase in dose. Following multiple administrations of 200 and 275 mg BID and 525 mg QD, steady-state plasma concentrations of Compound I were generally achieved within 2 days. On Day 7, following multiple BID dosing, there was some evidence of accumulation of Compound I, with a geometric mean $RA_{AUC}$ value of 1.1 following a 200 mg BID dose (ranging from 0.9 to 1.3), 1.5 (ranging from 1.1 to 1.9) at the 275-mg BID dose level, and 1.3 (range 1.0 to 1.6) at the 525-mg QD dose level. As expected for differing dosing regimens, higher trough concentrations were attained for BID dosing regimens compared to the QD regimen, with mean pre-dose Compound I concentrations on Day 7 being 1680, 3260, and 897 ng/mL for 200 mg BID, 275 mg BID, and 525 mg QD doses, respectively.

TABLE 5

Mean Pharmacokinetic Parameters of Compound I by Treatment Group
(Part B - Multiple Doses Administered Following a Low-fat Meal)

| | Dose of Compound I | | | |
|---|---|---|---|---|
| | 200 mg BID (B1) (N = 6) | | 525 mg QD (B2) (N = 6) | |
| Parameter | Day 1 | Day 7 | Day 1 | Day 7 |
| $AUC_{0-\tau}$ (hr*ng/mL) | 34900 (29.5)[a] | 38800 (27.3) | 78100 (31.3)[c] | 97800 (19.5) |
| $AUC_{0-\tau(norm)}$ (hr*ng/mL/(mg/kg)) | 11300 (34.1)[a] | 12600 (34.9) | 10500 (26.9)[c] | 13100 (14.8) |
| $C_{max}$ (ng/mL) | 6080 (20.7) | 6060 (20.1) | 8510 (16.2) | 9440 (10.8) |
| $C_{max\ (norm)}$ (ng/mL/(mg/kg)) | 1970 (30.5) | 1970 (28.5) | 1140 (11.3) | 1260 (11.6) |
| $t_{max}^{b}$ (hr) | 3.00 (2.00-4.00) | 4.00 (2.50-4.02) | 3.50 (1.50-4.00) | 3.53 (2.50-4.02) |
| $t_{1/2}$ (hr) | — | 4.89 (23.0)[b] | — | 6.25 (60.3)[c] |
| $\lambda_Z$ (hr$^{-1}$) | — | 0.142 (23.0)[b] | — | 0.0544 (107.5) |
| CL/F (mL/min) | — | 85.9 (27.3) | — | 89.4 (19.5) |
| $CL/F_{(norm)}$ ((mL/min)/kg) | — | 1.32 (34.9) | — | 1.27 (14.8) |
| $V_z/F$ (L) | — | 36.1 (33.7)[b] | — | 98.6 (112.1) |
| $V_z/F_{(norm)}$ (L/kg) | — | 0.576 (36.0)[b] | — | 1.40 (110.6) |
| $Ae_{0-12}$ (mg) | 105 (18.0) | 142 (15.2) | 171 (13.3) | 185 (27.1) |
| $Ae_{0-24}$ (mg) | — | — | 242 (7.2) | 284 (19.4) |
| $fe_{0-12}$ (%) | 52.5 (18.0) | 71.2 (15.2) | 32.6 (13.3) | 35.3 (27.1) |
| $fe_{0-24}$ (%) | — | — | 46.1 (7.2) | 54.0 (19.4) |
| $CL_R$ (mL/min) | 50.2 (45.4) | 61.2 (35.7) | 51.7 (31.8) | 48.3 (32.2) |
| $RA_{AUC}$ | — | 1.11 (13.3) | — | 1.25 (13.7) |

| | Dose of Compound I 275 mg BID (B3) (N = 6) | |
|---|---|---|
| Parameter | Day 1 | Day 7 |
| $AUC_{0-\tau}$ (hr*ng/mL) | 37700 (12.8)[d] | 56500 (13.4) |
| $AUC_{0-\tau(norm)}$ (hr*ng/mL/(mg/kg)) | 9560 (22.0)[d] | 14300 (35.9) |
| $C_{max}$ (ng/mL) | 6070 (11.6) | 7500 (10.9) |
| $C_{max\ (norm)}$ (ng/mL/(mg/kg)) | 1540 (18.2) | 1900 (30.5) |
| $t_{max}^{b}$ (hr) | 2.28 (1.50-4.00) | 2.75 (2.00-4.00) |
| $t_{1/2}$ (hr) | — | 5.64 (43.6) |
| $\lambda_Z$ (hr$^{-1}$) | — | 0.123 (43.6) |
| CL/F (mL/min) | — | 81.1 (13.4) |
| $CL/F_{(norm)}$ ((mL/min)/kg) | — | 1.16 (35.9) |
| $V_z/F$ (L) | — | 39.6 (39.3) |
| $V_z/F_{(norm)}$ (L/kg) | — | 0.568 (43.6) |
| $Ae_{0-12}$ (mg) | 162 (9.7) | 190 (13.1) |
| $Ae_{0-24}$ (mg) | — | — |
| $fe_{0-12}$ (%) | 58.9 (9.7) | 69.1 (13.1) |
| $fe_{0-24}$ (%) | — | — |
| $CL_R$ (mL/min) | 71.6 (17.9) | 56.1 (16.2) |
| $RA_{AUC}$ | — | 1.50 (19.1) |

$Ae_{0-12}$ = amount of GDC-3280 excreted over 12 hours; $Ae_{0-24}$ = amount of GDC-3280 excreted over 24 hours; $AUC_{0-\tau}$ = area under the concentration-time curve (AUC) during the dosing interval (τ or tau); $C_{max}$ = maximum observed plasma concentration; CL/F = apparent total clearance (GDC-3280 only); $CL_R$ = renal clearance; CV % = coefficient of variation; $fe_{0-12}$ = percentage of drug excreted in the first 12 hours; $fe_{0-24}$ = percent of GDC-3280 excreted over 24 hours; N = number of subjects; norm = body weigh-normalized value; $RA_{AUC}$ = accumulation ratio based on $AUC_{0-\tau}$; $t_{max}$ = time to maximum concentration; $t_{1/2}$ = apparent terminal elimination half-life; $V_z/F$ = apparent volume of distribution during the terminal elimination phase (GDC-3280 only); $\lambda_Z$ = apparent terminal elimination rate constant.
[a]Median (min-max).
[b]n = 5.
[c]n = 3.
[d]τ = 12 hours.
[e]τ = 24 hours.

Serum Creatinine (Scr) Observations

Figure 2:
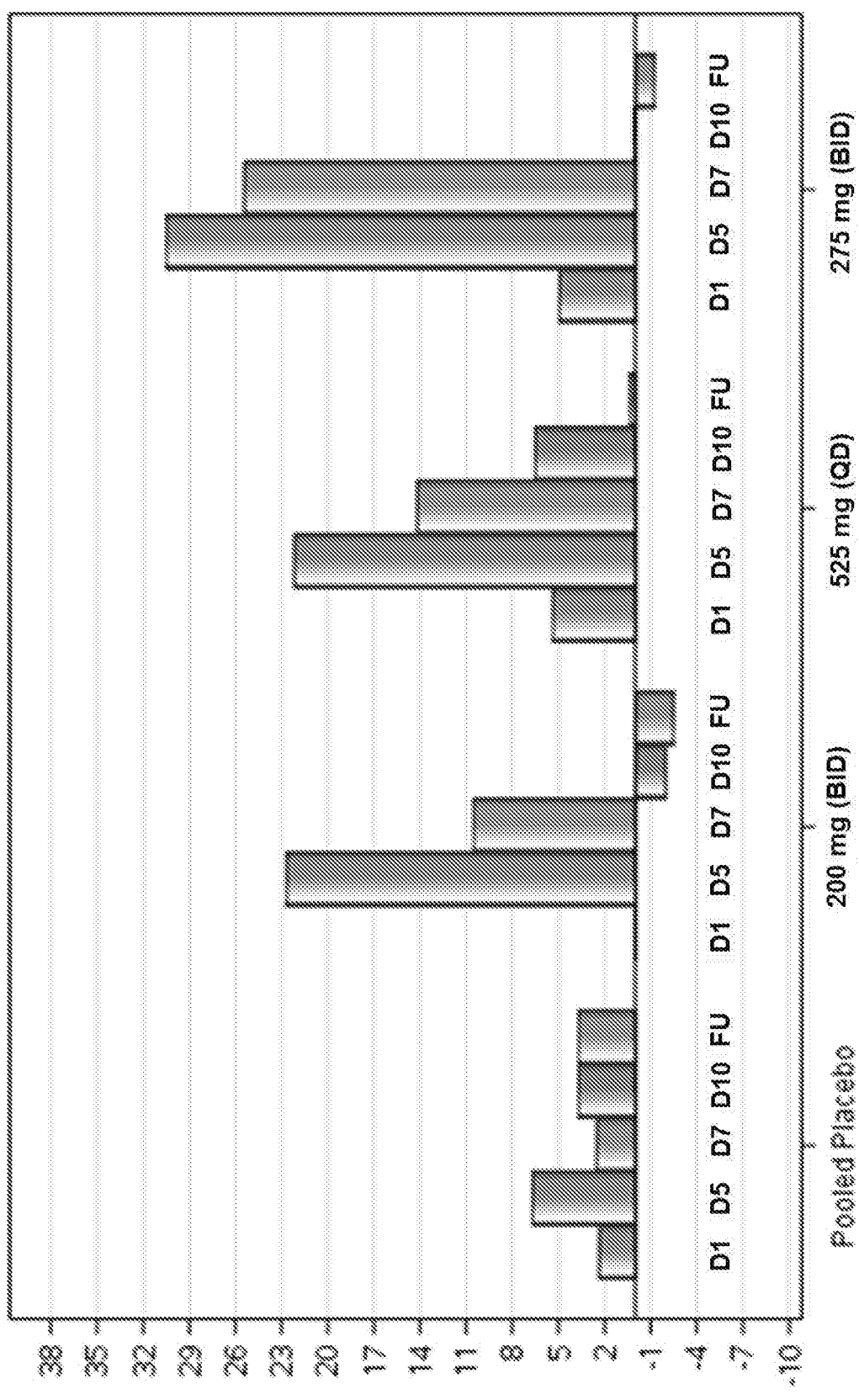
FIG. 2 illustrates the mean change in creatinine levels from screening level in the MAD part of the clinical study described herein. Analysis visits were on Day 1 (D1); Day 5 (D5); Day 7 (D7); Day 10 (D10) and at Follow Up (FU).

In addition to the measurement of various PK parameters in both parts of the study, the changes in the subjects' serum creatinine levels were also evaluated in this study. Tables 6A and 6B summarize the change in level and percent change in serum creatinine from averaged screening and pre-dosing values for the subjects in SAD study in each treatment group, as applicable. Tables 7A and 7B summarize the change in level and percent change in serum creatinine from averaged screening and pre-dosing values for the subjects in MAD study. Increases over the upper limit of normal (ULN) in serum creatinine were observed in both Part A (SAD) and Part B (MAD) of the study. In Part A of the study, changes were observed in about 21% of the exposures of doses of 200 mg or more. In Part B of the study, changes were observed in about 56% of the subjects across all dose levels. 25% percent of the subjects in MAD study had a mean change from baseline ≥0.3 mg/dL in Scr and 50% of the subjects in the MAD study had a mean percent change from baseline ≥30%. In Part B of the study, 2 subjects (275 mg BID) experienced clinically significant TEAEs of increased creatinine on day 5. The mean change in serum creatinine from a combined screening and pre-dose baseline in the MAD part of the study is illustrated in FIG. 1. In addition, the mean change in creatinine level from combined screening and pre-dose level in the MAD part of the study is illustrated in FIG. 2.

TABLE 6A

Change in Serum Creatinine level from baseline in SAD study

| Change in Ser | Placebo | 25 mg | 75 mg | 200 mg | 400 mg Fasted | 800 mg Fasted | 1600 mg | Total |
|---|---|---|---|---|---|---|---|---|
| Change < 0.3 mg/dL | 14 | 6 | 6 | 6 | 10 | 5 | 6 | 53 |
| Change ≥ 0.3 mg/dL | 0 | 0 | 0 | 0 | 2 | 1 | 0 | 3 |
| Total | 14 | 6 | 6 | 6 | 12 | 6 | 6 | 56 |

TABLE 6B

Percent Change in Serum Creatinine level from baseline in SAD study

| Percent Change in Scr | Placebo | 25 mg | 75 mg | 200 mg | 400 mg Fasted | 800 mg Fasted | 1600 mg | Total |
|---|---|---|---|---|---|---|---|---|
| Change < 30% | 14 | 6 | 6 | 6 | 9 | 4 | 6 | 51 |
| Change ≥ 30% | 0 | 0 | 0 | 0 | 3 | 2 | 0 | 5 |
| Total | 14 | 6 | 6 | 6 | 12 | 6 | 6 | 56 |

TABLE 7A

Change in Serum Creatinine level from baseline in MAD study

| Change in Scr | 400 mg (200 mg BID) | Placebo | 525 mg | 550 mg (275 mg BID) | Total |
|---|---|---|---|---|---|
| Change <0.3 mg/dL | 5 | 6 | 5 | 2 | 18 |
| Change ≥0.3 mg/dL | 1 | 0 | 1 | 4 | 6 |
| Total | 6 | 6 | 6 | 6 | 24 |

TABLE 7B

Percent Change in Serum Creatinine level from baseline in MAD study

| Percent Change in Scr | 400 mg (200 mg BID) | Placebo | 525 mg | 550 mg (275 mg BID) | Total |
|---|---|---|---|---|---|
| Change <30% | 1 | 6 | 3 | 2 | 12 |
| Change ≥30% | 5 | 0 | 3 | 4 | 12 |
| Total | 6 | 6 | 6 | 6 | 24 |

CONCLUSIONS

Compound I was rapidly absorbed in the fasted state following single oral doses of Compound I, with median $t_{max}$ values ranging from 1.3 to 2.5 hours. The geometric mean $t_{1/2}$ was similar for the 25 and 75 mg Compound I doses with a trend to increase with increase in dose ranging from 10.2 hours at the 200 mg dose level to 19.8 hours at the 1600-mg dose level.

Systemic exposure ($C_{max}$ and AUC) increased in a dose-proportional manner between 25 and 75 mg, and thereafter, less than proportional increases were observed for the 200-mg dose and greater. Between the 800 and 1600 mg dose there was no increase in AUC and $C_{max}$, reflecting saturable absorption. The less than proportional increase in systemic exposure was reflected by a dose-dependent decrease in the percent of Compound I excreted in urine (76.9% at 25 mg to 9.1% at 1600 mg).

In the low-fat fed state, Compound I was rapidly absorbed with $t_{max}$ values ranging from 1.0 to 4.0 hours. In the high-fat fed state, $t_{max}$ was increased, ranging from 1.5 to 6.0 hours. Administration of Compound I in a high-fat fed state led to 45.8% to 49.0% increases in $AUC_{0-\infty}$ and $AUC_{0-t}$, respectively, and a 68.9% increase in $C_{max}$ from the fasted state. Administration in the low-fat fed state also increased systemic exposure with 37.1%, 34.7%, and 64.4% increases in $AUC_{0-t}$, $AUC_{0-\infty}$, and $C_{max}$, respectively.

A drug-drug interaction with rabeprazole was observed as pretreatment and co-administration of 20 mg rabeprazole (QD×3) in the low-fat fed state led to a 23.5%, 22.8%, and 25.0% decrease in $AUC_{0-t}$, $AUC_{0-\infty}$, and $C_{max}$, respectively, compared to Compound I alone.

Following multiple dose administration of Compound I at 200 and 275 mg BID and 525 mg QD, steady-state was attained within 2 days. There was evidence of minimal accumulation by Day 7 (1.1- to 1.5-fold accumulation for BID and 1.3-fold for the QD regimen). Higher trough and lower peak concentrations were observed for BID compared to QD dosing regimens.

In Part B of the study, 2 subjects (275 mg BID) experienced clinical significant TEAEs of increased serum creatinine levels on day 5.

What is claimed is:

1. A method for providing oral Compound I therapy to a subject:

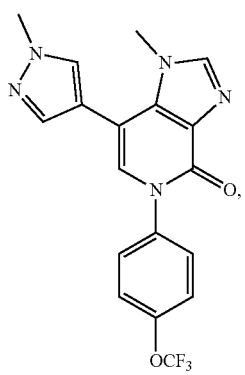

(Compound I)

comprising providing a therapeutically effective amount of Compound I to the subject; and advising the subject not to take a gastric acid reducing agent concomitantly with Compound I.

2. The method of claim 1, wherein the gastric acid reducing agent is selected from a proton pump inhibitor (PPI), a histamine 2 receptor antagonist (H2RA), or an antacid, or combinations thereof.

3. The method of claim 2, wherein the gastric acid reducing agent is a PPI.

4. The method of claim 3, wherein the PPI is rabeprazole.

5. The method of claim 1, further comprising advising the subject not to take the gastric acid reducing agent prior to or subsequent to taking the Compound I.

6. The method of claim 1, further comprising advising the subject to take the Compound I with food.

7. The method of claim 1, wherein the subject has an intra-gastric pH equal to or less than 4.

8. The method of claim 7, wherein the subject has an intra-gastric pH less than 3.

9. The method of claim 1, wherein the subject is in need of a gastric acid reducing agent.

10. The method of claim 1, comprising providing a Compound I to the subject at a dosage in a range of 1 mg to 5000 mg per day.

11. A method for providing oral Compound I therapy to a subject:

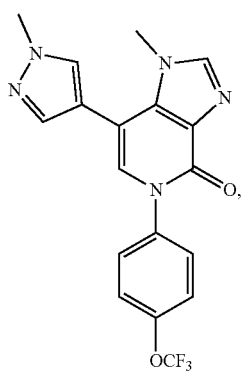

(Compound I)

comprising administering a therapeutically effective amount of Compound I to the subject and avoiding concomitant administration of a gastric acid reducing agent.

12. The method of claim 11, wherein the gastric acid reducing agent is selected from a proton pump inhibitor (PPI), a histamine 2 receptor antagonist (H2RA), or an antacid, or combinations thereof.

13. The method of claim 12, wherein the gastric acid reducing agent is a PPI.

14. The method of claim 13, wherein the PPI is rabeprazole.

15. The method of claim 11, comprising administering the Compound I with food.

16. The method of claim 11, wherein the subject has an intra-gastric pH equal to or less than 4.

17. The method of claim 16, wherein the subject has an intra-gastric pH less than 3.

18. The method of claim 11, wherein the subject is in need of a gastric acid reducing agent.

19. The method of claim 11, comprising providing a Compound I to the subject at a dosage in a range of 1 mg to 5000 mg per day.

20. A method for providing Compound I therapy to a subject in need thereof and in need of a gastric acid reducing agent:

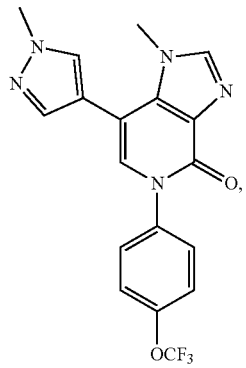

(Compound I)

comprising administering Compound I to the subject at a dosage of:

(i) 200 mg BID;

(ii) 525 mg QD; or (iii) 275 mg BID; and avoiding co-administration of a gastric acid reducing agent selected from a proton pump inhibitor (PPI), a histamine 2 receptor antagonist (H2RA), an antacid, or combinations thereof.

* * * * *